(12) United States Patent
Fujisaka et al.

(10) Patent No.: US 6,808,523 B2
(45) Date of Patent: *Oct. 26, 2004

(54) LASER THERAPEUTIC APPARATUS

(75) Inventors: Shinichi Fujisaka, Hamamatsu (JP); Sueo Miyaki, Hamamatsu (JP); Tsutomu Hara, Hamamatsu (JP); Koji Ichie, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 97 days.

This patent is subject to a terminal disclaimer.

(21) Appl. No.: 10/280,068

(22) Filed: Oct. 25, 2002

(65) Prior Publication Data

US 2003/0120325 A1 Jun. 26, 2003

Related U.S. Application Data

(63) Continuation-in-part of application No. PCT/JP01/03633, filed on Apr. 26, 2001.

(30) Foreign Application Priority Data

Apr. 27, 2000 (JP) .................................... P2000-127880

(51) Int. Cl.[7] .............................................. A61B 18/20
(52) U.S. Cl. ................................ 606/10; 606/2; 607/89
(58) Field of Search .................... 606/2–12; 607/88–94; 219/121.73

(56) References Cited

U.S. PATENT DOCUMENTS

| 5,514,127 | A | * | 5/1996 | Shanks ......................... 606/10 |
| 5,841,489 | A | * | 11/1998 | Yoshida et al. ................ 349/17 |
| 6,525,821 | B1 | * | 2/2003 | Thomas et al. .............. 356/457 |
| 6,710,292 | B2 | * | 3/2004 | Fukuchi et al. ......... 219/121.73 |

FOREIGN PATENT DOCUMENTS

| JP | 6-63164 | 3/1994 |
| JP | 11-221209 | 8/1999 |

* cited by examiner

Primary Examiner—Roy D. Gibson
Assistant Examiner—Henry M Johnson, III
(74) Attorney, Agent, or Firm—Morgan, Lewis & Bockius, LLP

(57) ABSTRACT

This apparatus includes a laser light source S2 which irradiates a spatial light modulator (SLM) 11 with a laser beam LR. Individual optical systems are arranged such that the laser beam reflected by the SLM 11 irradiates a region to be treated. When this configuration is used, the laser beam reflectivity can be made much higher than when a transmitting device is used. This allows high-efficiency laser beam irradiation. A predetermined pattern is written in the SLM 11, and this predetermined pattern is preferably a hologram pattern.

7 Claims, 9 Drawing Sheets

COMPUTER-SYNTHESIZED
HOLOGRAM

COMPUTER-SYNTHESIZED HOLOGRAM

LASER THERAPEUTIC APPARATUS

RELATED APPLICATION

This is a continuation-in-part application of application Ser No. PCT/JP01/03633 filed on Apr. 26, 2001, now pending.

BACKGROUND OF THE INVENTION

1. Field of the Invention

The present invention relates to a laser therapeutic apparatus for use in the field of laser therapies such as photodynamic therapy (PDT).

2. Related Background Art

With the recent progress of optical technologies, photodynamic therapy (PDT) has attracted attention. PDT is a therapeutic method which combines a laser and a photosensitive drug which specifically builds up in a proliferative tissue. By irradiating a lesion with a laser beam, a tumor tissue or neovascularization can be selectively destroyed or occluded without any thermal effect. For example, when a certain kind of photosensitive drug is administered to a patient beforehand and the lesion is irradiated with a laser beam, only tumor cells die with no influence on healthy cells. Also, it is being attempted to limit an irradiation region to a lesion by controlling the shape of a laser beam.

A laser therapeutic apparatus described in Japanese Patent Laid-Open No. 6-63164 is capable of controlling the shape of a laser beam and used in PDT. In this apparatus described in Japanese Patent Application Laid-Open No. 6-63164, a fluorescent image generated in a living body when the body is irradiated with a laser beam is sensed, the shape of a lesion is specified from the obtained fluorescent image, and a light transmitting region of a liquid crystal shutter is set in accordance with the specified shape. After that, the lesion is irradiated with a laser beam for treatment through the liquid crystal shutter. The liquid crystal shutter has a nematic liquid crystal or the like whose alignment direction changes depending on the applied voltage. By adjusting the applied voltage, therefore, the transmittance of a linearly polarized laser beam entering the liquid crystal can be controlled.

SUMMARY OF THE INVENTION

In the apparatus described in Japanese Patent Application Laid-Open No. 6-63164, however, the shape of a laser beam is controlled by passing the laser beam through the liquid crystal shutter. Accordingly, the transmittance is about 50% for a linearly polarized laser beam and about 25% for an unpolarized laser beam. The present invention has been made to solve the above problem, and has as its object to provide a laser therapeutic apparatus capable of emitting a laser beam at high efficiency.

To achieve the above object, a laser therapeutic apparatus of the present invention is a laser therapeutic apparatus for irradiating a region to be treated with a laser beam, comprising a reflecting spatial light modulator which displays a predetermined pattern, a laser light source which irradiates the spatial light modulator with a laser beam, and an optical system so positioned that the laser beam reflected by the spatial light modulator irradiates the region to be treated.

When the above configuration is used, the reflectivity of the laser beam can be well raised compared to an apparatus which uses a transmitting device, so laser beam irradiation can be performed at high efficiency.

The predetermined pattern is preferably a hologram pattern so set that in a region to be treated, the laser beam reflected by the spatial light modulator has the same shape as an image of this region to be treated. In this case, a totally reflected laser beam can be effectively used.

DESCRIPTION OF THE PREFERRED EMBODIMENT

Figure 1A:
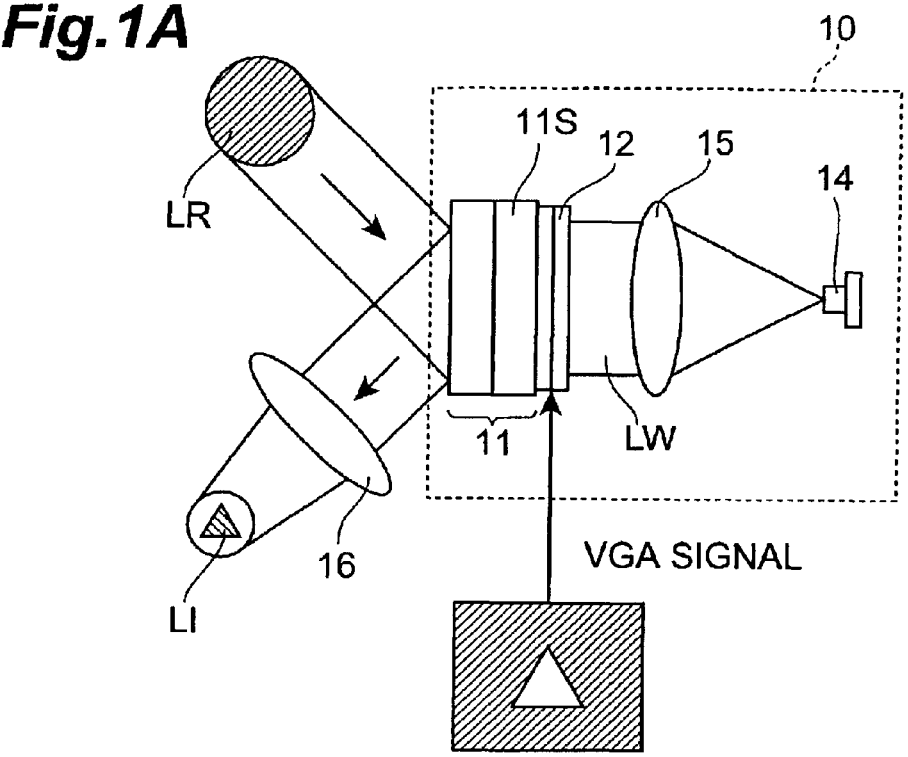
FIGS. 1A and 1B are views for explaining the main components of a laser therapeutic apparatus.

A laser therapeutic apparatus according to an embodiment will be described below. The same reference numerals denote the same parts, and a repetitive explanation will be omitted. This apparatus includes a reflecting spatial light modulator (SLM) and a liquid crystal display (LCD). These SLM and LCD will be described first.

Figure 13:
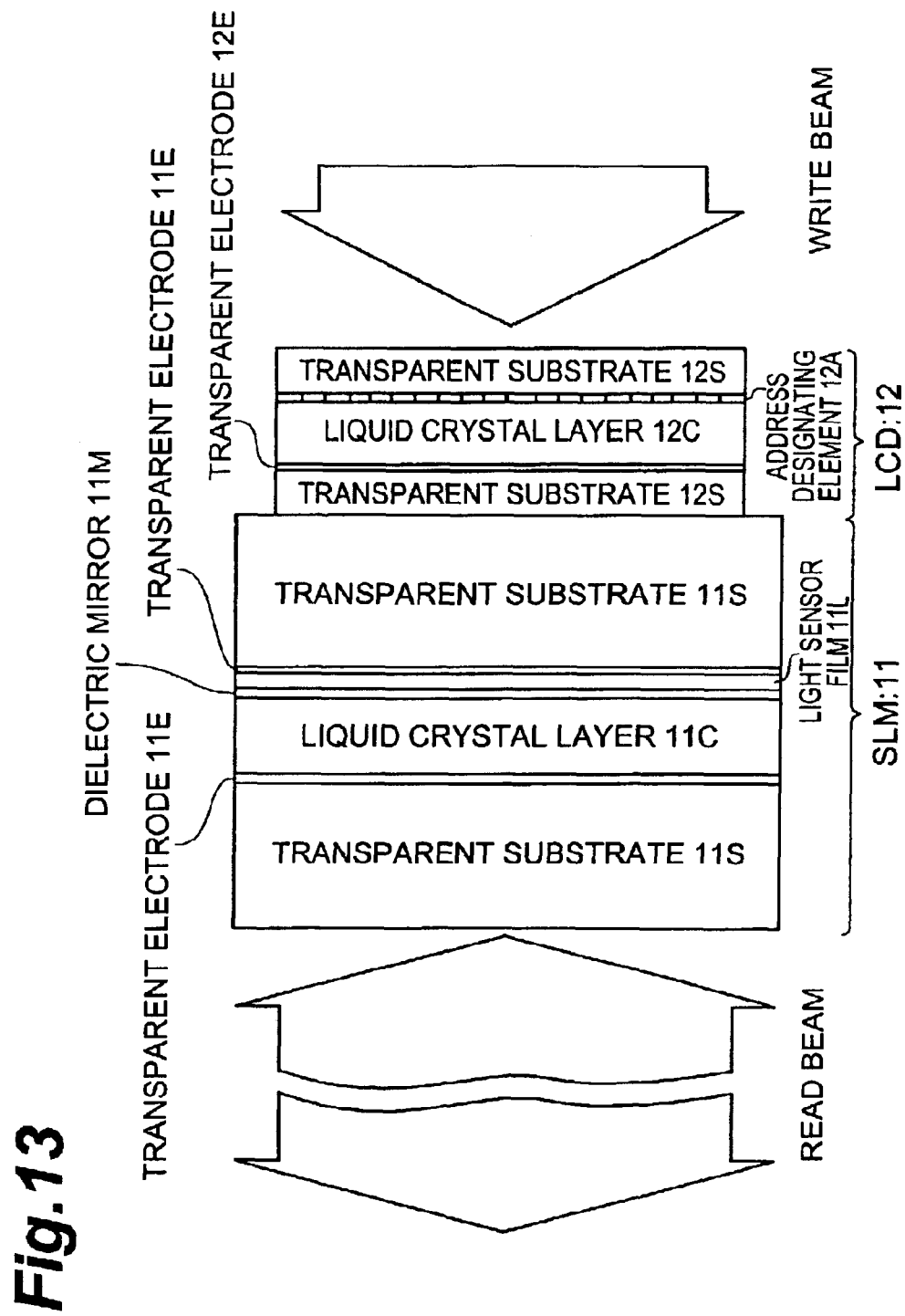
FIG. 13 is a view for explaining the structures of an SLM and an LCD.

FIG. 13 is a view for explaining the structures of the SLM and LCD.

An SLM 11 is a device which electro-optically records, reproduces, and erases two-dimensional images in real time, and has high optical information parallel processing capability. This SLM 11 has two transparent substrates 11S so formed that their transparent electrodes 11E oppose each other. A liquid crystal layer 11C is formed between these transparent substrates 11S. A light sensor film 11L is formed in contact with or close to the liquid crystal layer 11C. In addition, a dielectric mirror 11M is formed on one surface of the liquid crystal layer 11C. That is, five layers are formed between the transparent substrates 11S of this SLM 11.

An LCD 12 has a structure in which a liquid crystal layer 12C is formed between transparent substrates 12S, a transparent electrode 12E is formed on one surface of the liquid crystal layer 12C, and address designating elements 12A such as thin-film transistors (TFTs) are arranged on the other surface of the liquid crystal layer 12C. The transparent electrode is made of ITO (Indium Tin Oxide) or the like. The operations of these components will be explained below.

The LCD 12 gives a predetermined potential to a pixel electrode (TFT) at an address designated by the address designating element 12A. The voltage applied between the designated pixel electrode and the transparent electrode 12E changes the alignment state of the liquid crystal layer 12C. The address designating element 12A gives a potential corresponding to the luminance of a pixel forming a desired image to the corresponding pixel electrode in the LCD 12. Consequently, depending on the luminance of each pixel of the desired image, the alignment state of a portion corresponding to the pixel in the liquid crystal layer 12C changes. When the LCD 12 is irradiated with a write beam, the LCD 12 outputs a desired image displayed by the alignment state of the liquid crystal layer 12C. This output image from the LCD 12 is used as a write beam.

A voltage is applied to the liquid crystal layer 11C of the SLM 11 by the transparent electrodes 11E sandwiching this liquid crystal layer 11C, and the SLM 11 is irradiated with a write beam containing desired image information. Since the impedance of the light irradiation region in the light sensor film 11L lowers, the voltage applied to the liquid crystal layer 11C changes depending on the luminance of each pixel of the input image. Consequently, the display image on the LCD 12 is written in the SLM 11. Note that this "write" means display of an image to the SLM 11.

The light intensity transmitted through the liquid crystal layer '11C changes depending on the luminance of each pixel of the image written in the SLM 11. Therefore, when the liquid crystal layer 11C of the SLM 11 is irradiated with a read beam, this liquid crystal layer 11C modulates the luminance of the light for each pixel, and the dielectric mirror 11M reflects this luminance-modulated light. Consequently, the luminance-modulated light is output in a direction opposite to the irradiation direction. In this way, the display image on the LCD 12 is written in the SLM 11. After that, the SLM 11 is irradiated with a read beam, thereby irradiating a region to be treated with the reflected light whose luminance is modulated for each pixel. Note that the polarizing direction of the laser beam is so set as to achieve the above function.

A laser therapeutic apparatus using the SLM 11 and the LCD 12 will be explained below.

Figure 1B:
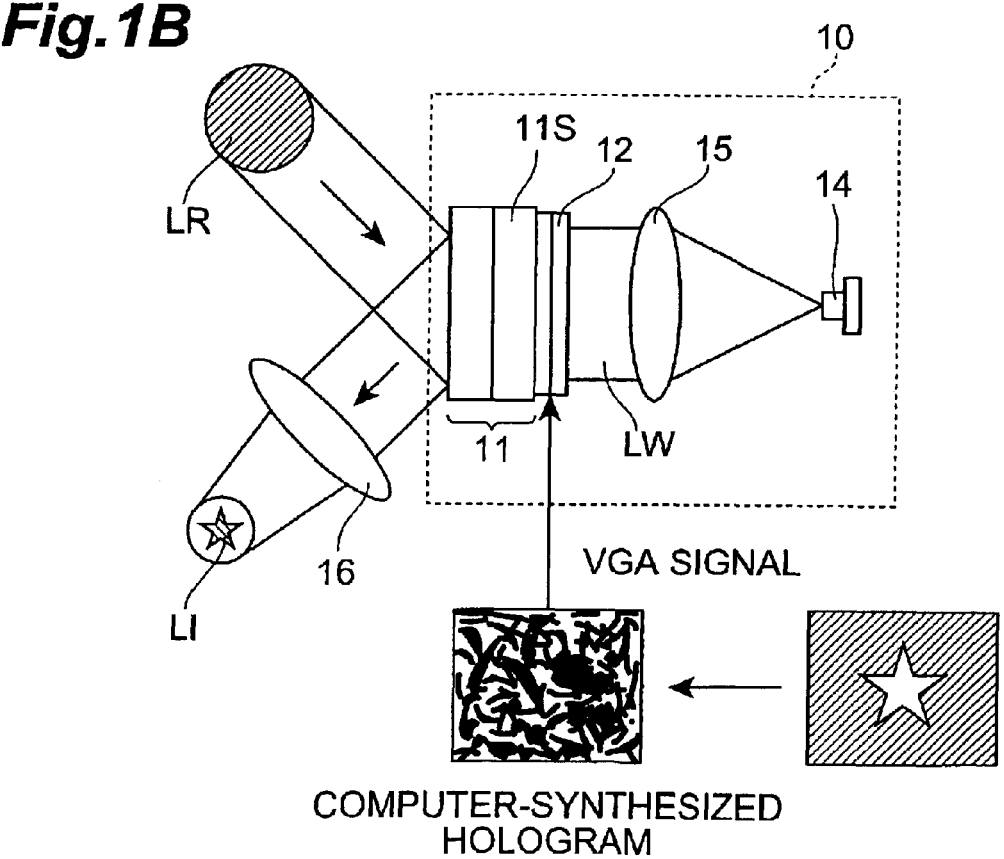

FIGS. 1A and 1B are views for explaining the major parts of this laser therapeutic apparatus. This apparatus has an SLM module 10 which includes the SLM 11 and the LCD 12 described above.

The SLM module 10 is an LCD-coupled reflecting SLM module which includes (A) an optical address type parallel aligned liquid crystal (PAL)-SLM 11, (B) an electrical address type LCD 12, (C) a write laser diode 14 for writing an image displayed on the LCD 12 into the PAL-SLM 11, and (D) a collimating optical system 15 which collimates a write laser beam emitted from the laser diode 14 into a parallel light beam and guides this parallel light beam onto the LCD 12. An image of the laser beam reflected by the SLM 11 is formed on a region to be treated by an image forming optical system 16. Referring to FIGS. 1A and 1B, the collimating optical system 15 is depicted as a single lens. However, this collimating optical system 15 is actually made up of a plurality of lenses for correcting aberration and the like.

One light transmitting substrate 11S forming the PAL-SLM 11 is replaced with an optical image transmitting device 11S such as an optical fiber plate (fiber optic plate (FOP)), and the spacing between the LCD 12 and this fiber plate 11S is properly set. In this manner, only image information displayed on the LCD 12 is transmitted, and the pixel structure of this LCD 12 is removed.

A VGA-standard image signal is input to the LCD 12. The data is written in the PAL-SLM 11 when this LCD 12 is irradiated with a laser beam (=write beam) LW from the laser diode 14.

FIG. 1A shows the case that data to be written is a normal image (in this example, a graphic image having a triangle in its center). When the PAL-SLM 11 is externally irradiated with a laser beam (=read beam) LR, spatial intensity modulation corresponding to intensity information of this image is performed for the read beam LR.

That is, the SLM module 10 functions as a variable masking means for the read beam LR.

In this example, the read beam LR is reflected by the PAL-SLM 11 and forms, through the lens 16, a reflected light image (projected pattern) LI, in which the intensity in a region except for a central triangular pattern is zero, on a region to be treated.

As shown in FIG. 1B, it is also possible to synthesize a Fourier transform hologram of a target pattern (in this example, a star shape) by a computer by using, e.g., the simulated annealing method, and write this hologram in the SLM module 10. When the PAL-SLM 11 is irradiated with the read beam LR, phase modulation corresponding to this computer-synthesized hologram is performed for the read beam LR.

In the method explained by using FIG. 1A, the PAL-SLM 11 is used as an intensity modulating device. According to the above explained method, the PAL-SLM 11 is used as a phase modulating device, so the entire light intensity of the read beam LR can be concentrated to the target pattern. Accordingly, the laser beam can be effectively used by minimizing the intensity loss. In this example, the read beam LR is reflected by the PAL-SLM 11 to form, through the lens 16, a reflected light image LI, in which the whole light beam is concentrated to the region of the star-shaped pattern, on a region to be treated. In this method, the lens 16 functions as a Fourier transform lens.

In the following embodiment, details of the latter method of writing a computer-synthesized hologram (hologram pattern) will be described first. In this embodiment, the aforementioned laser beam emitting apparatus is applied to a laser therapeutic apparatus for ophthalmology.

In the following explanation, it is assumed that proliferative neovascularization caused by age related macular degeneration (AMD) is obstructed by photodynamic therapy (PDT). PDT is a therapeutic method which combines a laser and a photosensitive drug which specifically builds up in a proliferative tissue, and can selectively destroy a tumor tissue or occlude neovascularization without any thermal effect.

Figure 2:
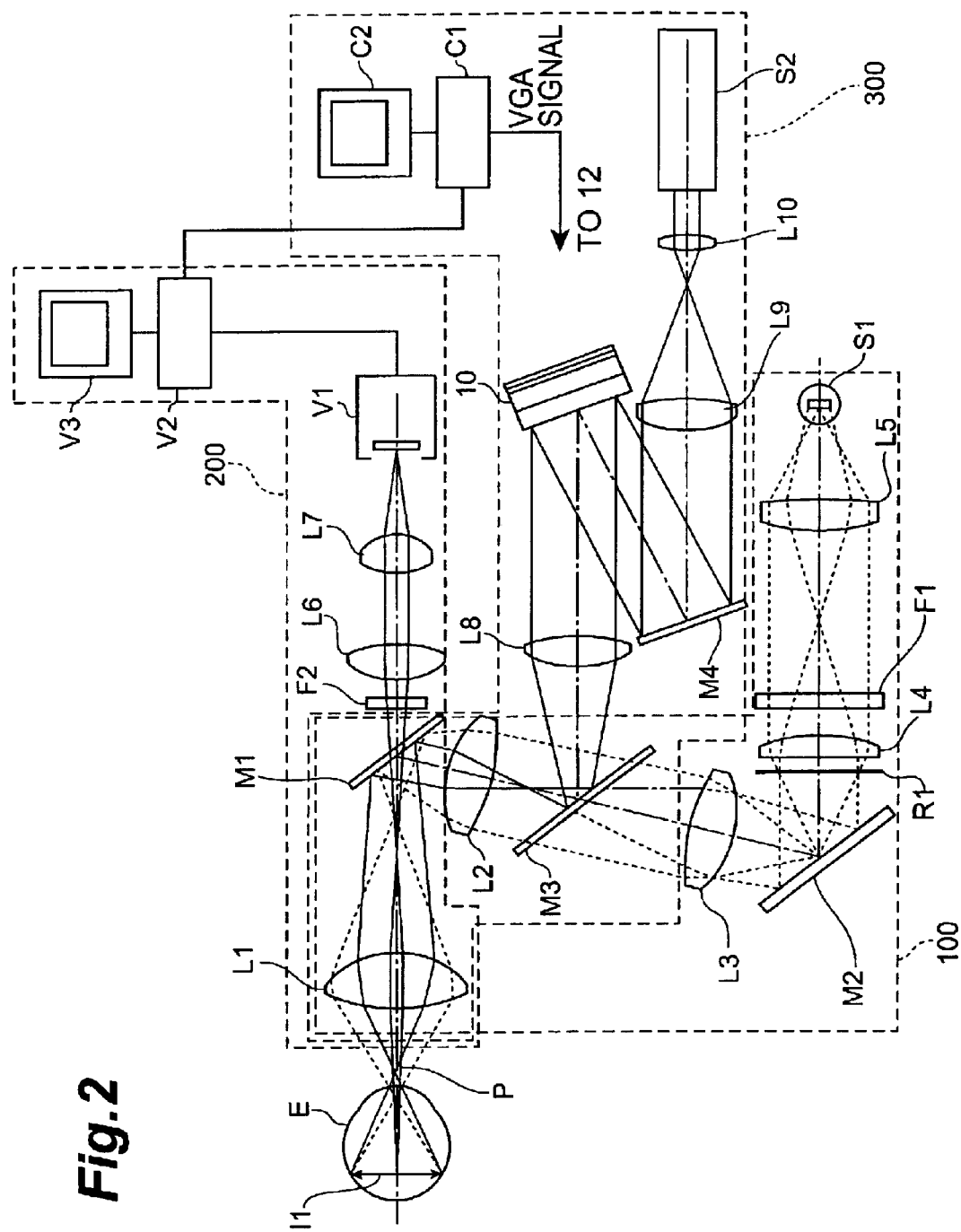
FIG. 2 is a view showing the system configuration of a laser therapeutic apparatus according to an embodiment.

FIG. 2 is a view showing the system configuration of a laser therapeutic apparatus according to this embodiment. This ophthalmologic laser therapeutic apparatus has an illuminating system 100 for illuminating the fundus of an eye E to be examined. The illuminating system 100 includes a light source S1 such as a halogen lamp and an illuminating optical system. In front of the light source S1, a lens L5, an exciting filter F1, a lens L4, a ring slit R1, and a mirror M2 are arranged along the optical axis. The exciting filter F1 can be inserted into and removed from the optical path as needed.

The exciting filter F1 may be an interference filter having transmitting wavelength characteristics including the absorption peak wavelength of a photosensitive substrate (to be described later). Additionally, a lens L3, a half mirror M3, a lens L2, and a mirror M1 are arranged along the optical axis of light reflected by the mirror M2.

A central portion of the mirror M1 is coated with a film which reflects only the wavelength of a laser (to be described later). The rest of this mirror M1 has a coating as an ordinary mirror. Furthermore, the back surface of the mirror M1 is coated with an antireflection film. The mirror M1 and the ring slit R1 are arranged in positions where they are substantially conjugate to the pupil of the eye E. An objective lens L1 is positioned on the optical axis of light reflected by the mirror M1.

In this illuminating system 100, light emitted from the light source S1 is incident on the mirror M2 via the lens L5, the exciting filter F1, the lens L4, and the ring slit R1. The light reflected by the mirror M2 is condensed by the lens L2 via the lens L3 and the half mirror M3, and incident on the mirror M1. The light reflected by the mirror M1 is condensed by the objective lens L1 to form an image in the position of the pupil of the eye E, thereby evenly irradiating the fundus from the perimeter of the pupil.

This ophthalmologic laser therapeutic apparatus is equipped with an observation system 200 which includes an observing optical system, a camera controller V2, and a monitor V3 to observe neovascularization on the fundus of the eye E. In this observing optical system, along the optical axis of the reflected light from the fundus of the eye E illuminated by the light source S1, a barrier filter F2, lenses L6 and L7, and a video camera V1 are arranged in addition to the objective lens L1 and the mirror M1 which form a part of the illuminating system 100 described above.

The barrier filter F2 cuts light (exciting light) transmitted through the exciting filter F1, and transmits fluorescence from a photosensitive substrate (to be described later). This barrier filter F2 can be inserted into and removed from the optical path where necessary. The barrier filter F2 is selected depending on the laser light source S2 or photosensitive drug used, because this barrier filter F2 cuts exciting light as mentioned above.

In this embodiment, a CCD camera is used as the video camera V1. This video camera V1 is connected to the camera controller V2 which is connected to the monitor V3. The camera controller V2 is also connected to an image processor C1 (to be described later).

When the eye E to be examined is placed in a predetermined position, light emitted from the light source S1 is reflected by the fundus of the eye E. The reflected light is condensed by the lens L7 via the objective lens L1, the mirror M1, the barrier filter F2, and the lens L6, thereby forming an image on the light-receiving surface of the CCD camera V1. This fundus image received by the CCD camera V1 is observed on the monitor V3 via the camera controller V2. Since the observation system 200 uses the barrier filter F2 as described above, only fluorescence is transmitted through this barrier filter F2. As a consequence, that portion of the fundus which emits fluorescence, i.e., a portion where a photosensitive drug exists is observed as a bright portion.

This ophthalmologic laser therapeutic apparatus further includes a light emitting system 300 which has a light emitting optical system for irradiating the fundus of the eye E with a laser beam, a laser light source S2, an SLM module 10, an image processor C1, and a monitor C2.

The laser light source S2 is appropriately selected in accordance with the absorption peak wavelength of a photosensitive drug (to be described later). In this embodiment, a laser diode is used as this laser light source S2. The use of the laser diode makes the apparatus compact and inexpensive. A lenses L10 and L9 and a mirror M4 are arranged along the optical axis of a laser beam emitted from the laser diode S2.

The laser beam reflected by the mirror M4 enters the SLM module 10 (a write optical system of the SLM module 10 is omitted in FIG. 2). A VGA signal from the image processor C1 is input to an LCD 12 of this SLM module 10. A lens L8 and a half mirror M3 are arranged along the optical axis of the laser beam reflected by the SLM module 10. A lens L2 and a mirror M1 are arranged along the optical axis of the laser beam reflected by the mirror M3. An objective lens L1 is positioned on the optical axis of the laser beam reflected by the mirror M1. The lens L2, the mirror M1, and the objective lens L1 form a part of the illuminating system 100 described above.

The laser beam emitted from the SLM module 10 is reflected by the half mirror M3 via the lens L8 and incident on the mirror M1 via the lens L2. The laser beam reflected by the mirror M1 is condensed by the objective lens L1, and an image of the original beam pattern (obtained if no modulation is performed) of this laser beam is formed as I1 on the fundus of the eye E (see FIG. 6 to be explained later). This beam pattern I1 matches the observation region of the fundus in the observation system 200. Also, the apparatus is so designed that a position P to which the laser beam is focused is located outside the cornea of the eye E as far as possible.

The operation procedure of the ophthalmologic laser therapeutic apparatus configured as above will be explained below. First, a specific photosensitive drug is injected intravenously into a patient. Although various substances can be used as this photosensitive drug, ATX-S10 (Photochemical Co., Ltd.) is used in this embodiment.

ATX-S10 has a characteristic feature of emitting fluorescence by specifically building up in a neoplastic substance. When the wavelength of exciting light is below 660 nm (preferably around 400 nm), fluorescence appears at 670 nm. Also, as the laser diode S2 for therapy described above, a laser having a wavelength of 670 nm and an output of a few ten mW to a few hundred mW is chosen.

Figure 3:
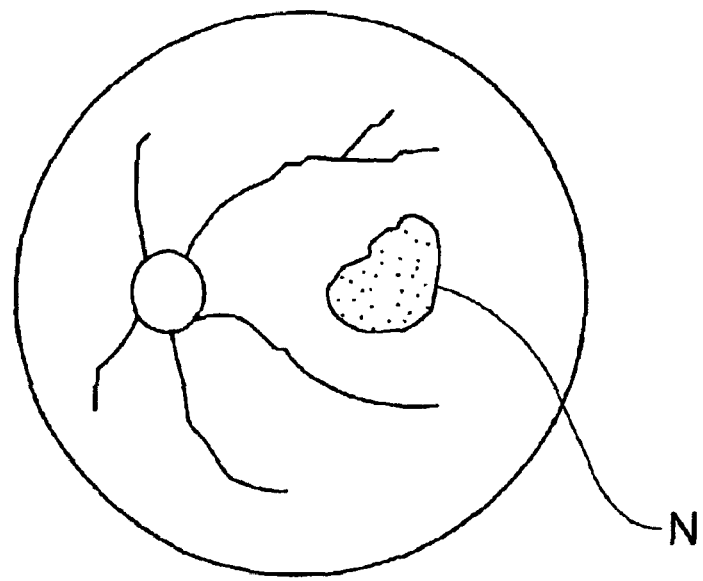
FIG. 3 is a view of a fundus image obtained by normal light.

After ATX-S10 is intravenously injected into a patient, the patient waits for about 30 min to 2 hr until ATX-S10 builds up in neovascularization. After the elapse of this predetermined time, the eye E to be examined is placed in a predetermined position of the apparatus. The light source S1 is turned on while the exciting filter F1 and the barrier filter F2 are not inserted into the optical path. The apparatus is so set that a focused fundus image of the eye E can be observed on the monitor V3 as shown in FIG. 3.

It is also possible to display the observed fundus image obtained by normal light on the monitor C2 via the image processor C1, and save the image in this image processor C1.

Figure 4:
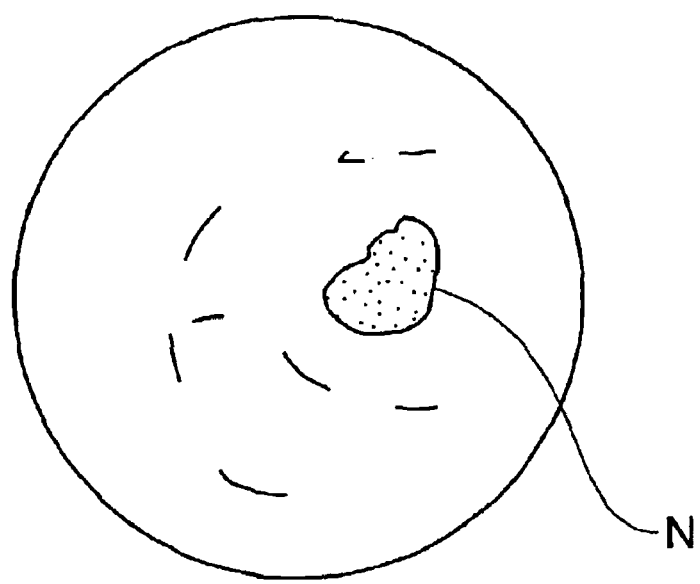
FIG. 4 is a view of a fluorescent image on the fundus.

After the apparatus is set, the exciting filter F1 and the barrier filter F2 suited to ATX-S10 are selected and inserted into the optical path. The exciting filter F1 which transmits light having a wavelength of below 660 nm (preferably around 400 nm) allows the light from the light source S1 to function as exciting light of ATX-S10. In addition, the barrier filter F2 which also transmits light having a wavelength of 670 nm extracts only fluorescence of the neovascularization in which ATX-10 built up. This fluorescence is displayed on the monitor V3 (FIG. 4).

Figure 5:
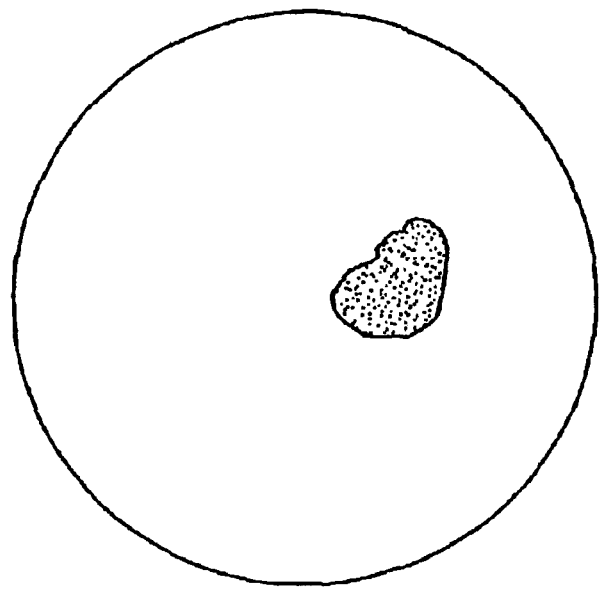
FIG. 5 is a view showing an image after the image shown in FIG. 4 is processed.

When the fluorescent image of the fundus is thus displayed, the image processor C1 freezes this image and displays the image on the monitor C2. An image processing function of the image processor C1 is used to extract the boundary of that region of the fundus which emits the fluorescence, i.e., a neovascularization region N, and erase pixel data except for this neovascularization region N (FIG. 5).

If necessary, the boundary and the like are manually corrected by using input means such as a mouse. It is also possible by using the above-mentioned image processing function to enhance or binarize the luminance of the neovascularization region N and thicken the boundary. The processed fluorescent image thus obtained is saved in the image processor C1. The monitor V3 keeps displaying the unprocessed fundus image in real time.

Note that the neovascularization region N, i.e., a region to be treated, is a region included in the eye E, and is also a region to be irradiated with a laser beam. This laser beam irradiation region can also be made larger than the region to be treated.

After the fluorescent image of the fundus is variously processed by using the image processor C1 and the monitor C2, the image processor C1 synthesizes a hologram (not shown) of the processed fluorescent image and outputs the image data as a VGA signal. Subsequently, the SLM module 10 is powered on.

Figure 6:
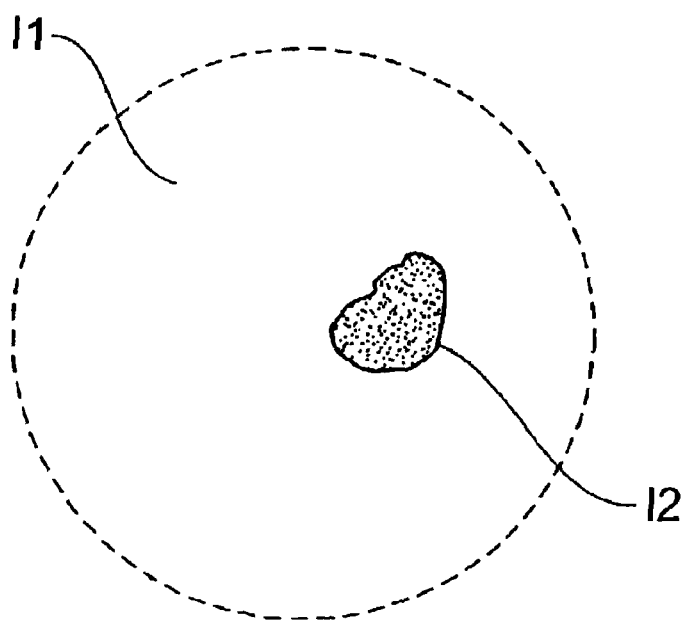
FIG. 6 is a view showing the beam pattern of a laser beam after modulation is performed using the image shown in FIG. 5.

Since the VGA signal from the image processor C1 is input to the LCD 12 of this SLM module 10, the write laser diode 14 writes the hologram described above (FIG. 1). Note that this laser diode 14 is not shown in FIGS. 2, 11, and 12. Then, the laser diode S2 is turned on to emit a laser beam. This laser beam is subjected to phase modulation by the SLM module 10 as described previously, and focused on the fundus of the eye E (FIG. 6).

In this state, the original beam pattern I1 (obtained if no modulation is performed) of this laser beam matches the observation region of the fundus, and an irradiation region I2 set by the SLM module 10 is irradiated in accordance with the position and shape of the neovascularization region N. The laser beam focuses its intensity on this neovascularization region N and has no intensity on other normal fundus portions, i.e., has no influence on these normal fundus portions. In this manner, ATX-S10 taken in the neovascularization and the laser beam specifically cause a photochemical reaction. This reliably occludes only the neovascularization.

If it is found by, e.g., observation of the fundus image displayed on the monitor V3 that the eye E has moved during laser beam irradiation, the laser diode S2 is once turned off. The current fundus image is displayed on the monitor C2 by the image processor C1, the processed fluorescent image saved beforehand is superposed and aligned on this current fundus image, and the current fundus image is erased. A hologram of the processed fluorescent image is again synthesized and written in the SLM module 10. After that, the laser diode S2 is turned on. In this way, laser beam irradiation corresponding to the neovascularization region N can be restarted.

In the above explanation, it is assumed that only one neovascularization region N is present on the fundus of the eye E to be examined. However, even if a plurality of neovascularization regions N are present, a plurality of irradiation regions can be set by the SLM module 10. So, these neovascularization regions N can be simultaneously treated within the procedure of the same one cycle as described above.

Also, as described previously, the SLM module 10 can also be used as a laser beam intensity modulating means, i.e., a masking means. In this case, the processed fluorescent image of the fundus is directly written in the SLM module 10 without synthesizing the hologram (this shortens the time required for hologram synthesis). The laser beam is subjected to spatial intensity modulation, i.e., masking, by the SLM module 10 as described above, and irradiates the fundus of the eye to be examined (FIG. 6). In this state, the original beam pattern I1 of this laser beam matches the observation region of the fundus, and the irradiation region I2 set by the masking by the SLM module 10 is irradiated in accordance with the position and shape of the neovascularization region N. After that, processing is performed in the same manner as when the hologram pattern is written in the SLM module 10.

A zooming optical system (not shown) can also be inserted into a portion where the observation system 200 and the light emitting system 300 share the optical path, i.e., between the mirror M1 and the objective lens L1. It is possible by this zooming optical system to observe only a region of interest of the fundus of the eye E by zooming the region, and irradiate this observation region with a laser beam having an original beam pattern matching the observation region. This zoom function is particularly effective when the SLM module 10 is used as a laser beam masking means. An operation procedure in this case will be explained below (the same contents as described above will be omitted).

Figure 7:
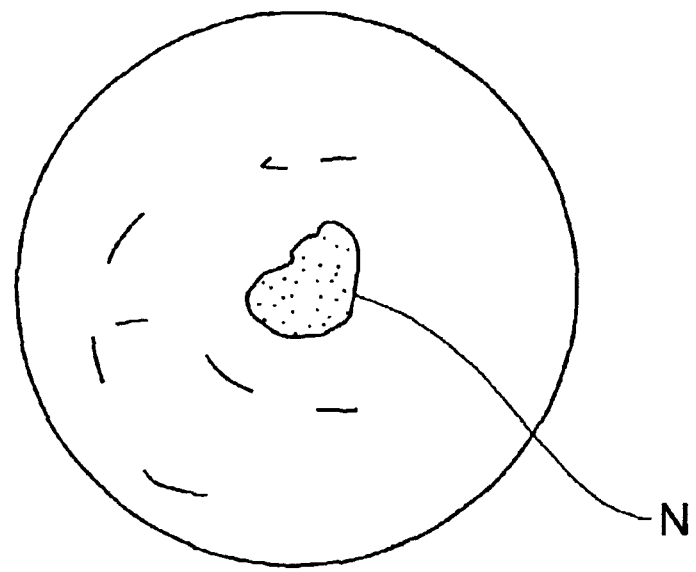
FIG. 7 is a view of a fluorescent image (guided around a neovascularization region) of the fundus.

First, without activating the zoom function, the fundus of the eye E to be examined is observed with normal light as shown in FIG. 3, and the exciting filter F1 and the barrier filter F2 are inserted to observe a fluorescent image of the fundus as shown in FIG. 4. Next, the eye E is guided using a fixation target or the like to position the neovascularization region N in a central portion of the image as close as possible (FIG. 7).

Figure 8:
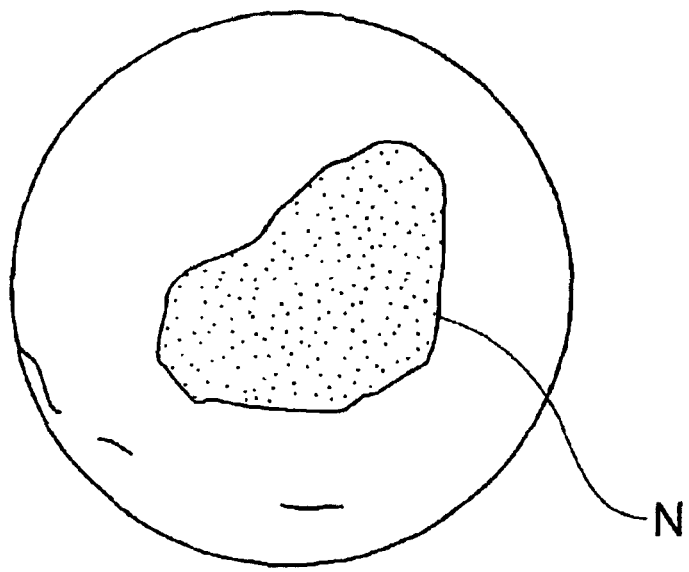
FIG. 8 is a view of a fluorescent image on the fundus after zooming.

The zoom function is then activated to observe the central portion including the neovascularization region N in an enlarged scale (FIG. 8).

Figure 9:
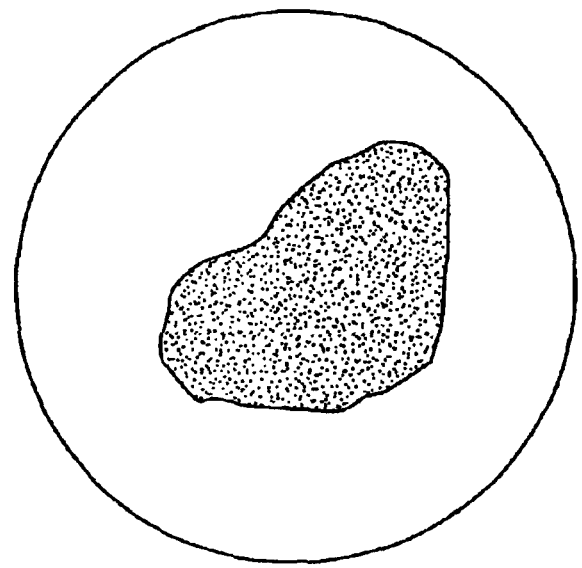
FIG. 9 is a view showing an image after the image shown in FIG. 8 is processed.

Subsequently, the image processor C1 is used to process this enlarged fluorescent image on the monitor C2 in the same manner as described above (FIG. 9). The processed fluorescent image is written in the SLM module 10, and the laser diode S2 is turned on.

Figure 10:
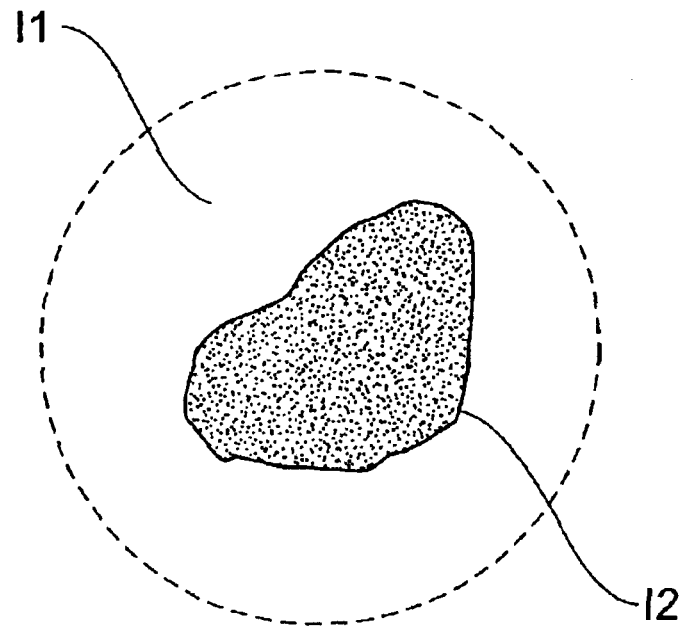
FIG. 10 is a view showing the beam pattern of a laser beam after modulation is performed using the image shown in FIG. 9.

The laser beam is masked by the SLM module 10 and irradiates the fundus of the eye E (FIG. 10).

In this state, the beam pattern I1 of this laser beam matches the enlarged observation region of the fundus, and the irradiation region I2 set by the masking by the SLM module 10 is irradiated in accordance with the position and shape of the neovascularization region N.

When this zoom function is used, the neovascularization region N occupies a wide region of the observed image. As a consequence, a region in which the intensity of the laser beam masked by the SLM module 10 is zero is made smaller than when no zoom function is used. Accordingly, the laser beam emitted from the laser diode S2 can be efficiently used in treatment.

The laser light source S2 is not restricted to a laser diode. For example, an excimer laser or an optical parametric oscillator (OPO) laser can also be used. Additionally, the laser beam emitted from this laser light source S2 can be guided by an optical fiber.

Figure 11:
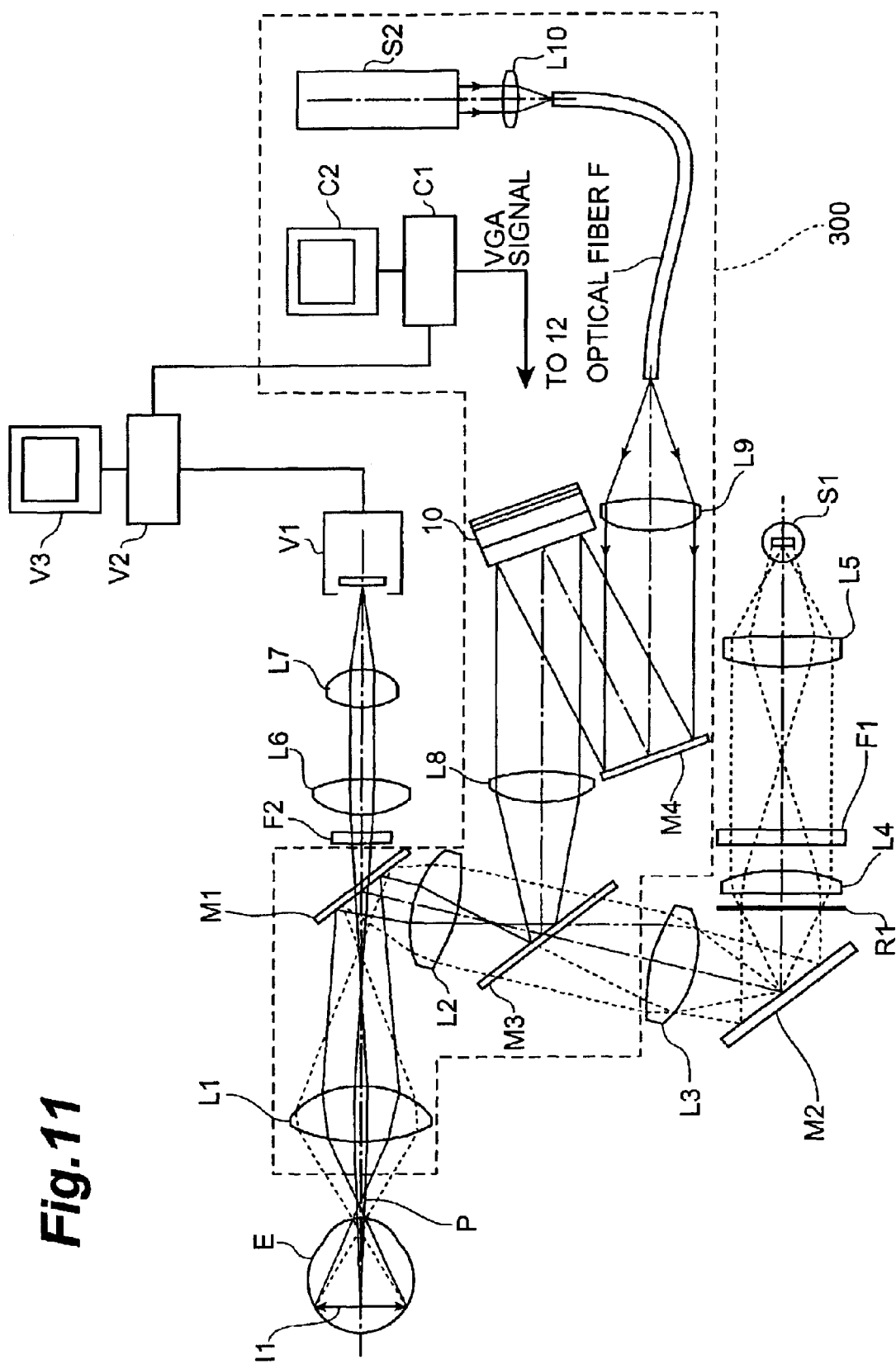
FIG. 11 is a view showing the system configuration of a laser therapeutic apparatus (using an optical fiber) according to another embodiment.

FIG. 11 is a view showing the system configuration of a laser therapeutic apparatus using light guiding by an optical fiber F. In this apparatus, a laser beam emitted from a light source S2 is condensed onto the input end of the optical fiber F by a condenser lens L10, output from the output end through the optical fiber F, and fed into a collimator lens L9. The rest of the arrangement is the same as shown in FIG. 2. When this optical fiber light guiding is used, a large laser device which cannot be installed in the apparatus main body can be used.

A light source S1 can be a laser diode or the like. When a laser diode is used, a photosensitive drug can be efficiently excited, and this facilitates observation of fluorescence of the fundus. In this case, an exciting filter F1 and a barrier filter F2 are selected depending on, e.g., the wavelength of this laser diode.

The optical intensity of the light source S1 when the fundus is observed with normal light without inserting any filter can be made different from that when fluorescence of the fundus is observed using exciting light by inserting the filters. By increasing the optical intensity of the light source S1 when fluorescence of the fundus is to be observed, a photosensitive drug can be efficiently excited, and this allows easy observation of fluorescence of the fundus.

The photosensitive drug is not limited to ATX-S10. For example, porfimer sodium or a benzoporphyrin derivative (BPD) can be used. When porfimer sodium is used, it takes 24 to 72 hr for this photosensitive drug to accumulate in neovascularization, so a laser light source S2 having a wavelength of 630 nm is chosen. When BPD is used, it takes 5 to 30 min for this photosensitive drug to accumulate in neovascularization, so a laser light source S2 having a wavelength of 690 nm is chosen.

In addition, when one of these photosensitive drugs is used, the exciting filter F1 and the barrier filter F2 are selected depending on, e.g., the fluorescent wavelength of the photosensitive drug.

In the above embodiment, the photosensitive drug is administered by intravenous injection. However, intra-arterial injection or dropping into the eye can also be used.

Furthermore, the half mirror M3 can be replaced with a flip mirror.

Figure 12:
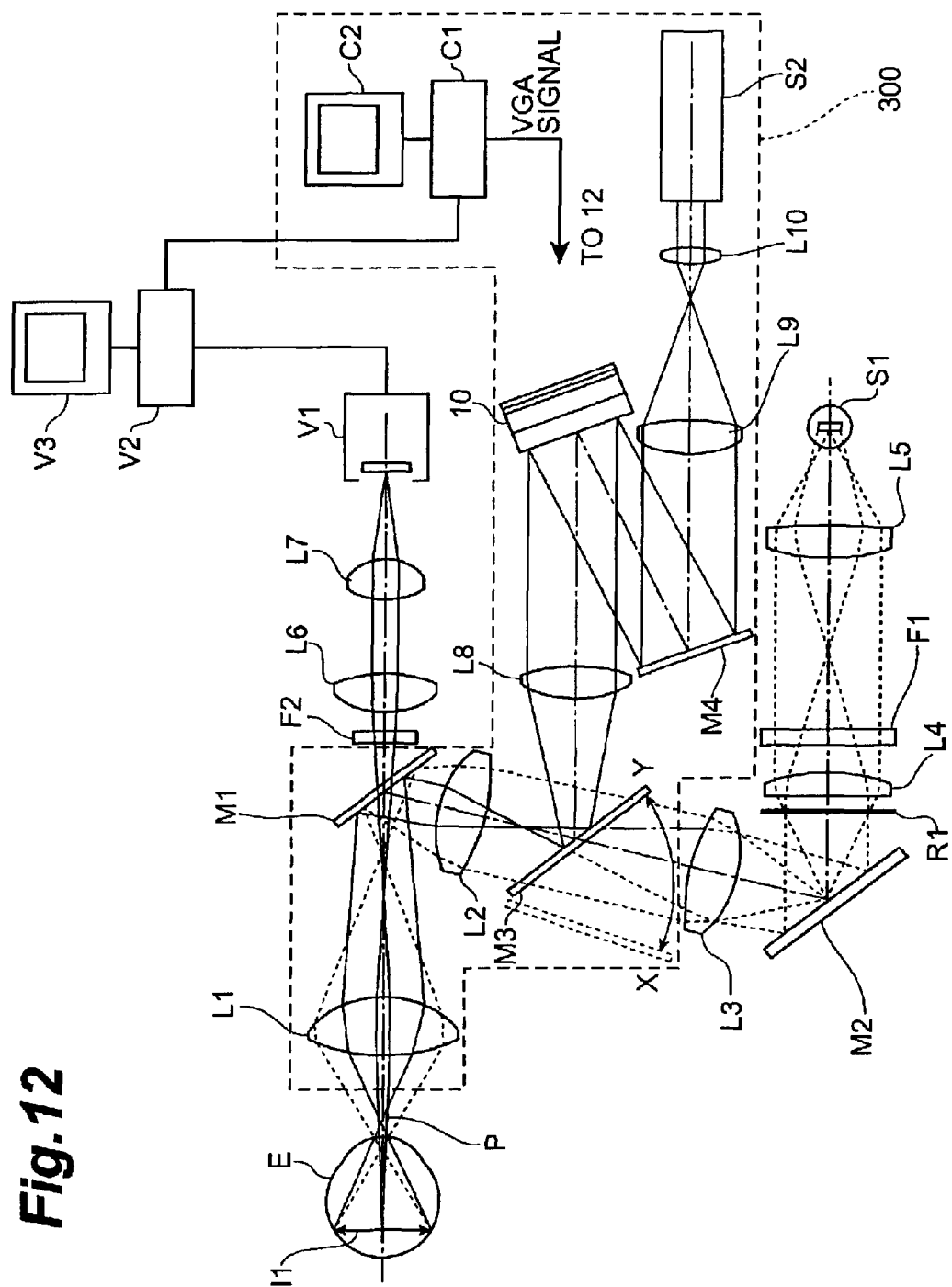
FIG. 12 is a view showing the system configuration of a laser therapeutic apparatus (using a flip mirror) according to still another embodiment.

FIG. 12 is a view showing the system configuration of a laser therapeutic apparatus using a flip mirror instead of the half mirror M3. When the fundus is to be observed by illumination of light from a light source S1, a flip mirror M3 is set in a position X. When a therapy is to be performed by irradiation with a laser beam from a laser light source S2, the flip mirror M3 is set in a position Y (the light from the light source S1 is interrupted). The rest of the arrangement is the same as in FIG. 2.

Although ophthalmologic laser therapeutic apparatuses have been explained as examples of the present invention, the present invention can be used in other applications, e.g., can be configured as laser therapeutic apparatuses for various tumors.

In the above laser therapeutic apparatus, a reflecting device (spatial light modulator) is used to set the irradiation region of a laser beam. Since the laser beam reflectivity is about 99%, the utilization efficiency of the laser beam is higher than in conventional apparatuses. Also, when a method of writing in this reflecting spatial light modulator a computer-synthesized hologram of an observation image containing a lesion is used, it is possible to utilize the light intensity of the laser beam in maximum eliminating a laser beam which is interrupted and hence is not used, thereby maximizing the light intensity of the laser beam. Since the spatial light modulator of this embodiment has no pixel structure, the utilization efficiency of the laser beam can be extremely raised. Eventually, the efficiency of 95% or more can be obtained when the reflectivity mentioned above is also taken into account.

As has been explained above, the laser therapeutic apparatus according to the above embodiment is a laser therapeutic apparatus for irradiating a region to be treated with the laser beam LI, characterized by comprising the reflecting spatial light modulator 11 which displays a predetermined pattern, the laser light source S2 which irradiates the spatial light modulator 11 with the laser beam LR, and the optical system 16 (i.e., L8, M3, L2, M1, and L1) so positioned that the laser beam reflected by the spatial light modulator 11 irradiates the region to be treated. When this configuration is used, the reflectivity of the laser beam can be made much higher than when a transmitting device is used. Accordingly, laser beam irradiation can be performed at high efficiency.

The predetermined pattern is preferably a hologram pattern so set that in a region to be treated, the laser beam reflected by the spatial light modulator 11 has the same shape as an image of this region to be treated. In this case, a totally reflected laser beam can be effectively used.

With reference to FIG. 1, in the above-mentioned apparatus, the LCD 12 for displaying the pattern is placed adjacent to the SLM 11. The laser beam LR emitted from the light source 14 (FIG. 1) irradiates the spatial light modulator 11 via the LCD 12, thereby writing the pattern in the SLM 11. In this way, the pattern is displayed on the SLM 11.

As shown in FIG. 13, the SLM 11 includes the light sensor film 11L in which the impedance of a region irradiated with light lowers, the transparent electrode 11E which transmits a laser beam, the liquid crystal layer 11C interposed between the light sensor film 11L and the transparent electrode 11E, and the dielectric mirror 11M which reflects a laser beam.

The laser therapeutic apparatus also includes the illuminating system 100 for illuminating the fundus of the eye E, and the observation system 200 for observing the fundus.

The observation system 200 includes the optical filter L2 which transmits only fluorescence emitted from the fundus.

This observation system 200 further includes the video camera V1 for sensing a fluorescent image from the fundus. On the basis of this fluorescent image sensed by the video camera V1, the aforementioned predetermined pattern displayed on the SLM 11 is generated.

In the apparatus shown in FIG. 11, a laser beam is transmitted between the light source S2 and the SLM 11 by using an optical fiber.

In the apparatus shown in FIG. 12, the illuminating light from the illuminating system and the laser beam from the light source S2 are selectively guided to the fundus by using the flip mirror M3 which is movably placed in the common path of these light components.

What is claimed is:

1. A laser therapeutic apparatus for irradiating a region to be treated with a laser beam, comprising:
    a reflecting spatial light modulator which displays a predetermined pattern;
    a first laser light source which irradiates said spatial light modulator with a laser beam; and
    an optical system so positioned that the laser beam reflected by said spatial light modulator irradiates the region to be treated.

2. A laser therapeutic apparatus according to claim 1, wherein the predetermined pattern is a hologram pattern so set that in the region to be treated, the laser beam reflected by said spatial light modulator has the same shape as an image of the region to be treated.

3. A laser therapeutic apparatus according to claim 1, wherein a liquid crystal display for displaying the pattern is placed adjacent to said spatial light modulator, and a laser beam emitted from a second light source different from said first light source irradiates said spatial light modulator via said liquid crystal display to write the pattern in said spatial light modulator, thereby displaying the pattern on said spatial light modulator.

4. A laser therapeutic apparatus according to claim 3, wherein said spatial light modulator comprises a light sensor film in which the impedance of a region irradiated with light lowers, a transparent electrode which transmits a laser beam, a liquid crystal layer interposed between said light sensor film and said transparent electrode, and a dielectric mirror which reflects a laser beam.

5. A laser therapeutic apparatus according to claim 1, further comprising an illuminating system which illuminates the region to be treated, and an observation system which observes the region to be treated.

6. A laser therapeutic apparatus according to claim 5, wherein said observation system comprises an optical filter which transmits only fluorescence emitted from the region to be treated.

7. A laser therapeutic apparatus according to claim 5, wherein said observation system comprises a video camera which senses a fluorescent image from the region to be treated, and the predetermined pattern displayed on said spatial light modulator is generated on the basis of the fluorescent image sensed by said video camera.

* * * * *